United States Patent
Yanaihara et al.

(10) Patent No.: US 6,399,318 B1
(45) Date of Patent: Jun. 4, 2002

(54) IMMUNOASSAY FOR PHTHALIC ACID ESTERS

(75) Inventors: Noboru Yanaihara, Shizuoka; Ikuo Kato, Fujinomiya; Shingo Nagasawa, Fuji; Tsukasa Kodaira, Itano-gun, all of (JP)

(73) Assignees: Otsuka Pharmaceutical Co., Ltd., Tokyo-To; Yanaihara Institute Inc., Shizouka-ken, both of (JP)

( * ) Notice: Subject to any disclaimer, the term of this patent is extended or adjusted under 35 U.S.C. 154(b) by 0 days.

(21) Appl. No.: 09/984,451

(22) Filed: Oct. 30, 2001

(30) Foreign Application Priority Data

Nov. 10, 2000 (JP) .......................... 2000-343565
Apr. 24, 2001 (JP) .......................... 2001-125609

(51) Int. Cl.$^7$ ...................... G01N 33/532; C07K 16/44; C07K 17/06
(52) U.S. Cl. ...................... 435/7.93; 435/7.5; 436/544; 436/815; 530/389.8; 530/405
(58) Field of Search .............. 530/389.8, 405; 435/7.5, 7.93; 436/544, 815

(56) References Cited

PUBLICATIONS

Lloyd et al, J. Nat'l. Medical Assoc., 83(10), 901–904 (1991).*
Bankert et al, Transplantation Proceedings, XII(3), 409–412 (1980).*
Bankert et al, Immunol. Commun., 10(6), 457–481 (1981).*
Bodmer et al, *J. Steroid biochem.*, 33(6):1161–1166 (1989).
Meyer et al, *J. Steroid Biochem.*, 35(2):263–269 (1990).
Tiefenauer et al, *J. Steroid Biochem.*, 35(6):633–639 (1990).

* cited by examiner

*Primary Examiner*—Mary E. Ceperley
(74) *Attorney, Agent, or Firm*—Sughrue Mion, PLLC

(57) ABSTRACT

The present invention provides an immunoassay for phthalic acid esters, which comprises measuring the phthalic acid esters contained in a sample using an antibody produced with a conjugate of a carrier protein and a phthalic acid ester derivative represented by the formula

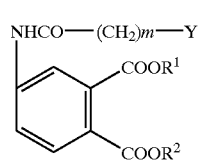

(1)

wherein $R^1$ and $R^2$ may be the same or different and are hydrogen, alkyl, cycloalkyl or phenylalkyl, with the proviso that both of $R^1$ and $R^2$ are not hydrogen; m is an integer from 1 to 5; and Y is amino or carboxyl.

5 Claims, 3 Drawing Sheets

IMMUNOASSAY FOR PHTHALIC ACID ESTERS

FIELD OF THE INVENTION

The present invention relates to an immunoassay for phthalic acid esters.

BACKGROUND OF THE INVENTION

Phthalic acid esters are chemicals widely used as plasticizers in the manufacturing of plastic products.

Recently, it has been confirmed that phthalic acid esters disrupt the endocrinal system of living organisms, and the leaching phthalic acid esters from plastic products has been recognized as a serious environmental pollution problem.

So far the detection and measurement of phthalic acid esters have been carried out by high performance liquid chromatography, LC-Mass spectrometry, GC-Mass spectrometry and like general methods. However, such methods entail high machinery costs and can test only a limited number of samples. Also, their detection and measurement capability is limited. Therefore, the development of a simple, convenient method capable of precisely detecting and measuring phthalic acid esters in a large number of samples has been desired.

An object of the present invention is to solve the prior art problem and provide a simple, convenient detection and measurement method for phthalic acid esters and means for the detection and measurement.

SUMMARY OF THE INVENTION

The inventors succeeded in creating an immunoassay system capable of achieving the object and accomplished the present invention.

The present invention provides the following antigens, anti-phthalic acid ester antibodies, biotinylated phthalic acid ester derivatives, and immunoassays for phthalic acid esters utilizing the antibody or the antibody and the biotinylated derivative.

(1) An antigen for the production of an anti-phthalic acid ester antibody, which comprises a conjugate of a carrier protein and a phthalic acid ester derivative represented by the formula

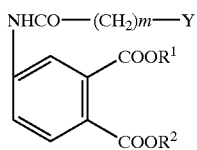
(1)

wherein $R^1$ and $R^2$ may be the same or different and are hydrogen, alkyl, cycloalkyl or phenylalkyl, with the proviso that both of $R^1$ and $R^2$ are not hydrogen; m is an integer from 1 to 5; and Y is amino or carboxyl.

(2) An anti-phthalic acid ester antibody produced using the antigen defined in item (1).

(3) A biotinylated phthalic acid ester derivative represented by the formula

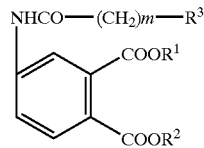
(2)

wherein $R^1$, $R^2$ and m are as defined above and $R^3$ is biotin-$(R^4)_n$—NH— or —CO—$(R^4)_n$—NHNH-biotin wherein the $R^4$s may be the same or different and are an Arg residue or a Lys residue, and n is an integer from 1 to 3.

(4) A method for assaying phthalic acid esters in a sample by an immunoassay technique, which comprises measuring the phthalic acid esters contained in the sample using the anti-phthalic acid ester antibody defined in item (2).

(5) The method according to item (4) wherein the immunoassay technique utilizes the biotinylated phthalic acid ester derivative of item (3) as a labeled compound.

BRIEF DESCRIPTION OF THE DRAWINGS

In the specification, the accompanying drawings are referred to, wherein.

DETAILED DESCRIPTION OF THE INVENTION

Figure 1:
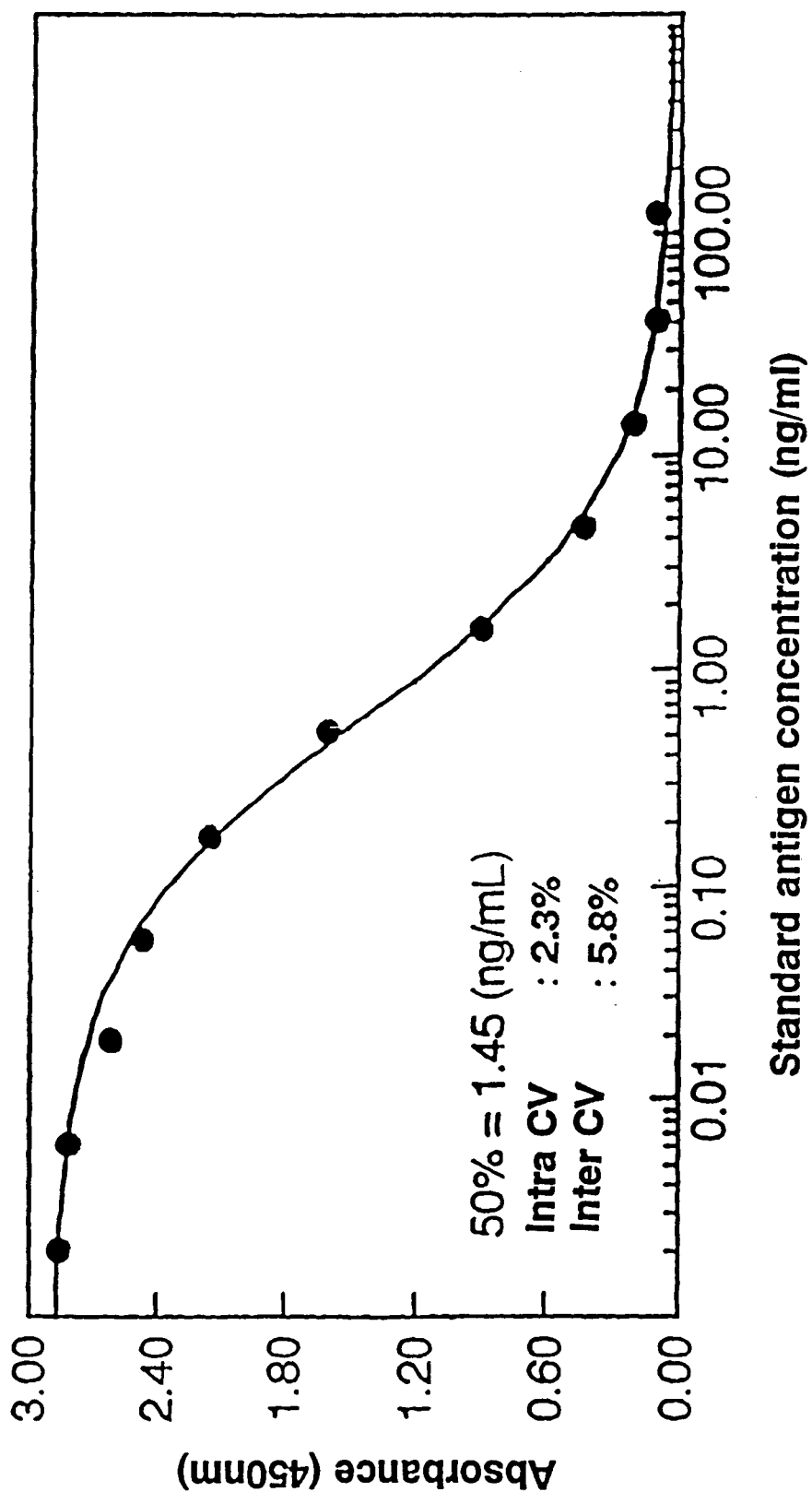
FIG. 1 is an enzyme immunoassay standard curve for diethyl phthalate.

The antigens of the invention include the phthalic acid ester derivatives of formula (1); and the biotinylated phthalic acid ester derivatives of the invention are represented by formula (2).

Examples of groups represented by $R^1$ and $R^2$ in formulas (1) and (2) are shown below.

Examples of alkyl groups include $C_{1-10}$ straight or branched chain alkyl groups such as methyl, ethyl, propyl, isopropyl, n-butyl, tert-butyl, pentyl, hexyl, heptyl, octyl, nonyl, decyl, 2-ethylhexyl and the like.

Examples of cycloalkyl groups include $C_{3-8}$ cycloalkyl groups such as cyclopropyl, cyclobutyl, cyclopentyl, cyclohexyl, cycloheptyl, cyclooctyl and the like.

Examples of phenylalkyl groups include phenylalkyl groups which have 1 to 6 carbon atoms in the alkyl moiety. Specific examples are benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl and the like.

In the biotinylated phthalic acid ester derivative of formula (2), biotin in the group represented by $R^3$ is conjugated via a bond of its side chain CO group to the amino acid residue ($R^4$) or —NHNH—. The amino acid residue ($R^4$) includes D-isomers and L-isomers, unless otherwise specified.

Antigen of the Invention

The antigen of the invention comprises a conjugate of a phthalic acid ester derivative of formula (1) and a carrier protein.

The phthalic acid ester derivatives of formula (1) include monoesters and diesters. The diesters have two ester forming groups, such as alkyl, cycloalkyl or like groups, which may be identical or different.

The phthalic acid ester derivatives can be prepared by conventional methods. For example, a commercially available phthalic anhydride is nitrated and hydrolyzed and then esterified to produce a nitro phthalic acid ester. Subsequently, the nitro compound is reduced to obtain the corresponding amino compound (4-aminophthalic acid) using, for example, tin and hydrochloric acid. Then a spacer (e.g., aminocaproic acid) represented by HOOC—$(CH_2)_m$—Y (wherein Y and m are as defined above) is conjugated to the amino compound to give the desired phthalic acid ester derivative of formula (1).

The amino compound and reactions for its synthesis are known or can be performed according to known methods (see, for example, CA Registration No. 22572-84-5 J. Med. Chem., 30, 509–514 (1987)). The conjugation reaction of the amino compound with the spacer can be carried out, for example, by a condensation reaction as will be described later in the manufacturing process for biotinylated phthalic acid ester derivatives.

The amino compound used for producing the phthalic acid ester derivatives can be prepared, for example, by the process shown in Reaction Scheme-1.

[Reaction Scheme-1]

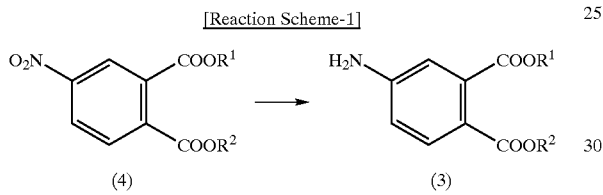

wherein $R^1$ and $R^2$ are as defined above.

The conversion of compound (4) into compound (3) as shown in Reaction Scheme-1 is carried out, for example, by one of the following reactions:
  (a) reducing compound (4) in a suitable solvent using catalytic reduction; or
  (b) reducing compound (4) in an inert solvent using as a reducing agent a mixture of a metal or metal salt and an acid, or a mixture of a metal or metal salt and an alkali metal hydroxide, sulfide or ammonium salt.

When reaction (a) is carried out, useful solvents include water, acetic acid and like lower alkanoic acids; methanol, ethanol, isopropanol and like alcohols; hexane, cyclohexane and like hydrocarbons; dioxane, tetrahydrofuran (THF), diethyl ether, diethylene glycol dimethyl ether and like ethers; methyl acetate, ethyl acetate and like esters; N,N-dimethylformamide (DMF) and like aprotic polar solvents; and mixtures of these solvents.

Useful catalysts for catalytic reduction include palladium, palladium-black, palladium-carbon, platinum, platinum oxide, copper chromite, Raney nickel and the like. These catalysts are preferably used in an amount of 0.02 to 1 times the weight of the starting compound (4).

The reaction is usually carried out at about −20° C. to about 150° C., to about 100° C., under a hydrogen pressure of, preferably, about 1 to about 10 atm. The reaction is usually completed in about 0.5 to about 10 hours. Optionally, acids such as hydrochloric acid may be added to the reaction system.

When reaction (b) is carried out, useful inert solvents include water, acetic acid and like lower alkanoic acids; methanol, ethanol and like alcohols; benzene, toluene, xylene and like aromatic hydrocarbons; dioxane and like ethers; and mixtures of these solvents.

Useful reducing agents include mixtures of iron, zinc, tin or tin chloride and a mineral acid such as hydrochloric acid or sulfuric acid; and mixtures of iron, ferrous sulfate, zinc or tin and an alkali metal hydroxide (e.g., sodium hydroxide), sulfite (e.g., ammonium sulfide), aqueous ammonia or ammonium salt (e.g., ammonium chloride).

The conditions for the reduction reaction can be decided according to the type of reducing agent used. For example, when the reducing agents are zinc and hydrochloric acid, the reaction efficiently proceeds at 0° C. to room temperature and is completed in about 0.5 to about 15 hours. Zinc and hydrochloric acid are both usually used in an equimolar to 20-fold molar amount, relative to the compound (4).

The compound (4) used as a starting material in Reaction Scheme-1 can be prepared, for example, by the processes shown in Reaction Scheme-2 to Reaction Scheme-4.

[Reaction Scheme-2]

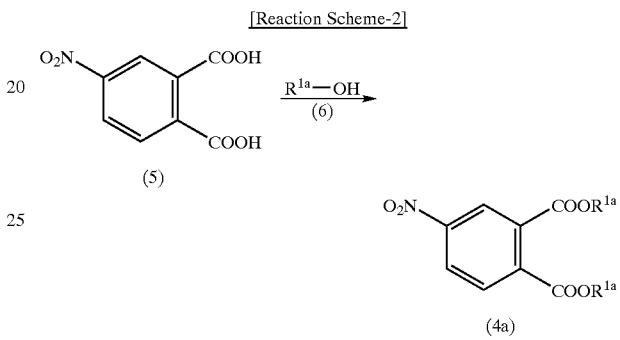

wherein $R^{1a}$ is alkyl, cycloalkyl or phenylalkyl.

The reaction between compound (5) and compound (6) in Reaction Scheme-2 can be carried out in the presence of a mineral acid such as hydrochloric acid or sulfuric acid and a halogenating agent such as thionyl chloride, phosphorus oxychloride, phosphorus pentachloride or phosphorus trichloride at 0° C. to about 200° C., preferably about 50° C. to about 150° C. Preferably, compound (6) is used in a large excess amount, relative to compound (5).

[Reaction Scheme-3]

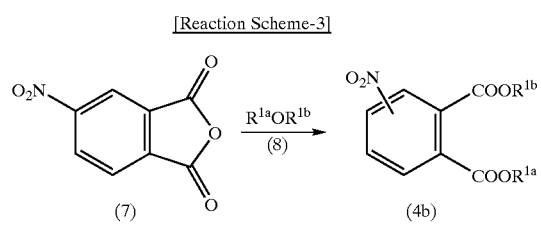

wherein $R^{1a}$ is as defined above, $R^{1b}$ is hydrogen or alkali metal; compound (4b) is substituted by a nitro group at the 4- or 5-position on the benzene ring.

Examples of alkali metals include sodium and potassium.

The reaction between compound (7) and compound (8) in Reaction Scheme-3 is carried out in a suitable inert solvent or without using any solvents, in the presence or absence of a basic compound.

Examples of useful inert solvents include benzene, toluene, xylene and like aromatic hydrocarbons; THF, dioxane, diethylene glycol dimethyl ether and like ethers; dichloromethane, chloroform, tetrachloromethane and like halogenated hydrocarbons; methanol, ethanol, isopropanol, butanol, tert-butanol, n-hexanol and like alcohols; acetic acid and like lower alkanoic acids; ethyl acetate and like esters; acetone and like ketones; acetonitrile, pyridine, DMSO, N,N-dimethylformamide (DMF), hexamethylphosphoric triamide (HMPA) and like aprotic polar solvents; and mixtures of these solvents.

Examples of useful basic compounds include sodium carbonate, potassium carbonate, sodium hydrogencarbonate, potassium hydrogencarbonate and like carbonates; sodium hydroxide, potassium hydroxide and like alkali metal hydroxides; sodium hydride; potassium; sodium amide; sodium methylate, sodium ethylate and like metal alcoholates; pyridine, N-ethyl diisopropylamine, dimethylaminopyridine, triethylamine, 1,5-diazabicyclo [4.3.0]nonene-5(DBN), 1,8-diazabicyclo[5.4.0] undecene-7 (DBU), 1,4-diazabicyclo[2.2.2]octane(DABCO) and like organic bases.

Compound (8) is used at least in an equimolar amount, preferably in an equimolar to about 10-fold molar amount, relative to compound (7). The reaction is carried out usually at 0° C. to about 200° C., preferably 0° C. to about 150° C., and is usually completed in about 5 minutes to about 3 hours.

[Reaction Scheme-4]

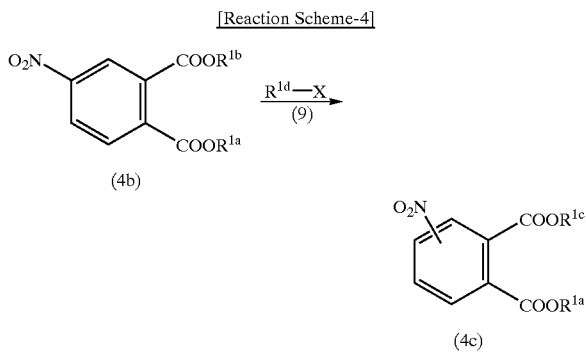

(4b)

(4c)

wherein $R^{1a}$ and $R^{1b}$ are as defined above, $R^{1c}$ is alkyl, cycloalkyl or phenylalkyl; X is halogen or hydroxyl; compound (4c) is substituted by a nitro group at the 4- or 5-position on the benzene ring.

Useful halogens are fluorine, chlorine, bromine and iodine.

In Reaction Scheme-4, the reaction between compound (4b) and compound (9) wherein X is halogen is carried out in a suitable inert solvent in the presence of a basic compound.

Examples of useful inert solvents include benzene, toluene, xylene and like aromatic hydrocarbons; THF, dioxane, diethylene glycol dimethyl ether and like ethers; dichloromethane, chloroform, tetrachloromethane and like halogenated hydrocarbons; methanol, ethanol, isopropanol, butanol, tert-butanol, n-hexanol and like alcohols; acetic acid and like lower alkanoic acids; ethyl acetate and like esters; acetone and like ketones; acetonitrile, pyridine, DMSO, DMF, HMPA and like aprotic polar solvents; and mixtures of these solvents.

Examples of useful basic compounds include sodium carbonate, potassium carbonate, sodium hydrogencarbonate, potassium hydrogencarbonate and like carbonates; sodium hydroxide, potassium hydroxide and like alkali metal hydroxides; sodium hydride; potassium; sodium amide; sodium methylate, sodium ethylate and like metal alcoholates; pyridine, N-ethyl diisopropylamine, dimethylaminopyridine, triethylamine, DBN, DBU, DABCO and like organic bases.

Compound (9) is used at least in an equimolar amount, preferably in an equimolar to about 3-fold molar amount, relative to compound (4b). The reaction is carried out usually at 0° C. to about 200° C., preferably 0° C. to about 170° C., and is usually completed in about 5 minutes to about 10 hours.

The reaction between compound (4b) wherein $R^{1b}$ is alkali metal and compound (9) wherein X is hydroxyl can be carried out in a suitable inert solvent or without using any solvents, in the presence of an acid.

Useful inert solvents include those mentioned above in the reaction between compound (4b) and compound (9) wherein X is halogen.

Useful acids include mineral acids such as hydrochloric acid and sulfuric acid.

Compound (9) is used at least in an equimolar amount, preferably in an equimolar to about 3-fold molar amount, relative to compound (4b). The reaction is carried out usually at 0° C. to about 200° C., preferably 0° C. to about 170° C., and is usually completed in about 5 minutes to about 10 hours.

The reaction between compound (4b) wherein $R^{1b}$ is hydroxyl and compound (9) wherein X is hydroxyl can be carried out in a manner similar to the reaction between compound (5) and compound (6) shown in Reaction Scheme-2, under similar conditions.

The phthalic acid ester derivative of formula (1) is conjugated to a carrier protein by a condensation reaction using a conventional reagent so as to form a peptide bond between the functional group Y of formula (1) and the carboxyl or amino group of the carrier protein.

Useful carrier proteins include any carrier proteins conventionally used in the field to enhance the immunogenicity of an antigen or a haptene. Examples of carrier proteins include albumin, globulin, hemocyanin and like various animal proteins; and polylysine and like artificial polypeptides.

The reagent used for the condensation reaction may be selected from various known reagents. Preferable reagents are 1-(3-dimethylaminopropyl)-3-ethyl carbodiimide hydrochloride (WSCD) and like water-soluble carbodiimides, dimethyl suberimidate (DMS) and like condensing agents.

To produce an anti-phthalic acid ester antibody of the present invention, the conjugate of the phthalic acid ester derivative and carrier protein may be used as it is, or the conjugate may be adsorbed onto an appropriate polymer adsorbent and the resulting adsorbent can be used as the antigen.

Useful polymer adsorbents include various polymers conventionally used in the field to enhance immunogenicity. Such polymers include, for example, carbon powders, polyvinylpyrrolidone, latexes, porcine thioglobulin and like serum proteins. The polymer adsorbent is combined with the antigen of the invention in a conventional manner.

Antibody of the Invention

The antibody of the invention can be produced by immunizing warm-blooded animals (except for humans) using the antigen of the invention according to a general antibody production method. Conventional methods and means and modifications thereof can be used. The antibody of the invention includes polyclonal antibodies such as antiserums of warm-blooded animals and chicken egg antibodies, and monoclonal antibodies.

Polyclonal antibodies can be produced, for example, in the following manner. The antigen of the invention in combination with Freund's complete adjuvant is inoculated several times into a warm-blooded animal such as a rabbit, sheep, guinea pig, or chicken to immunize the animal. Then the blood is collected and antiserum is obtained from the blood by a conventional method. When chickens are used, polyclonal antibodies can also be obtained by inoculating a hen with the antigen several times and producing eggs in which immunoglobulin (IgY) has been produced. Then IgY is isolated from the egg yolk using a conventional method.

Monoclonal antibodies can be produced, for example, in the following manner. Mice are immunized several times with the antigen of the invention in combination with Freund's complete adjuvant. The resulting antibody-producing cells are fused with splenic cells or bone marrow cells using a conventional method such as the cell fusion method. Then, a clone which produces the desired antibody is selected from the cell library and cultured.

The antibodies (polyclonal antibodies and monoclonal antibodies) can be further purified according to conventional methods such as salting out using ammonium sulfate, ion exchange chromatography, gel chromatography and affinity chromatography.

It is important to select an antibody which specifically reacts with the desired phthalic acid ester but does not substantially crossreact with other phthalic acid esters.

Such an antibody can be selected with good precision by testing the reactivity of antibodies obtained from immunized warm-blooded animals or clones to various phthalic acid esters according to the method disclosed in this specification.

Any reactivity test can be used without limitation, as long as the test confirms the immunoreactivity between the antibody of the invention and the test compound. The reactivity test is preferably carried out, for example, by the immunoassay methods described below in Examples.

When an antibody is produced using an antigen selected from phthalic acid ester derivatives of formula (1), the antibody specifically reacts with the phthalic acid ester corresponding to the selected phthalic acid ester derivative. That is, the obtained antibody is reactive to a specific side chain region of phthalic acid esters. Such side chain region-specific reactive antibodies include, for example, antibodies which specifically react with dimethyl phthalate, diethyl phthalate, di-n-butyl phthalate, di(2-ethylhexyl)phtalate, diisobutyl phtalate, benzyl n-butyl phthalate or the like. Preferably used are antibodies which specifically react with one phthalic acid ester and do not substantially crossreact with other phthalic acid esters having similar side chain structure. However, antibodies which crossreact with some other phthalic acid esters may also be used, if so desired.

The phrase "not substantially crossreact" means that the cross-reactivity does not exceed 5%, preferably 1% or less, relative to the reactivity with a specific phthalic acid ester (calculated as 100%).

Detection and Measurement of Phthalic Acid Ester

Phthalic acid esters can be detected and measured by immunoassay techniques utilizing the antibody of the invention.

Useful immunoassay techniques include, for example, enzyme immunoassay (EIA), enzyme linked immunosolvent assay (ELISA), fluorescent immunoassay (FIA) and luminescent immunoassay. Methods such as the competitive method or the sandwich method may also be used.

The immunoassay for phthalic acid esters of the invention is preferably carried out using a highly sensitive ELISA system as described below in Examples.

The antibody of the invention to be used in the highly sensitive ELISA system is selected according to the target phthalic acid ester. That is, an antibody which specifically reacts with the phthalic acid ester to be measured is used as the antibody. An immobilized antibody is usually used. In this system, the target phthalic acid ester can be utilized as a standard substance.

A biotinylated phthalic acid ester derivative of formula (2) is advantageously used as a labeled antigen (labeled compound) in the highly sensitive ELISA. Its preparation process will be described below. The derivative corresponding to the target phthalic acid ester is selectively used.

The biotinylated phthalic acid ester derivatives of formula (2) are generally soluble in the liquid phase used in the immunoassay system (they are water soluble). Therefore, these derivatives are highly useful as labeled compounds in the phthalic acid ester immunoassay system.

The immunoassay of the invention realizes a highly sensitive immunoassay of various phthalic acid esters, with a minimum detectable level of about 50–100 pg/ml, as described below in Examples.

The detection and measurement of phthalic acid esters according to the invention can be expediently carried out by utilizing an immunoassay kit containing the antibody of the invention as an active ingredient. The immunoassay kit may contain, in addition to the antibody of the invention, other reagents necessary for detection and measurement. Examples of such reagents include the aforementioned labeled compound (labeled antigen) and standard antigen. The kit may further contain assay buffer solutions, etc.

The immunoassay of the present invention is useful for the detection and measurement of phthalic acid esters in test samples such as tissues, blood, urine, bone marrow fluid and saliva of humans and other mammals. The results can be utilized to study the influence of the endocrine disrupting chemicals on living organisms.

The immunoassay of the invention can also detect and measure phthalic acid esters in the environment such as in river water, lake water, sea water, waste water, air, soil and the like, thereby determining the level of pollution.

Biotinylated Phthalic Acid Ester Derivative

The biotinylated phthalic acid ester derivative of formula (2), which can be used as a labeled compound in the immunoassay of the invention, can be prepared by using a phthalic acid ester derivative of formula (1) as a starting material and conjugating thereto a biotin-amino acid conjugate selected from biotin-$(R^4)_n$—OH and H—$(R^4)_n$—NHNH-biotin wherein $R^4$ and n are as defined above.

The conjugation can be carried out, for example, by sequential condensation of 1–3 amino acids (Arg and Lys) represented by $R^4$ and biotin or its hydrazine with the phthalic acid ester derivative, or by a condensation reaction between a previously condensed biotin-amino conjugate and the phthalic acid ester derivative.

Useful condensation methods include known methods such as the azide method, mixed acid anhydride method, DCC method, activated ester method, oxidation-reduction method, DPPA (diphenylphosphoryl azide) method, DCC+ additive method (additives: 1-hydroxybenzotriazole, N-hydroxysuccinimide, N-hydroxy-5-norbornene-2,3-dicarboximide, etc.), and Woodward method.

The solvent used in such condensation methods can be suitably selected from a variety of solvents conventionally used in such peptide condensation reactions. Examples of useful solvents include N-methylpyrrolidone (NMP), DMF, DMSO and mixed solvents thereof.

The functional groups not involved in the condensation reaction can be protected with generally used protective groups according to conventional methods, and the protective groups can be removed after completion of the reaction. These reaction methods are known, and suitable reagents for use in these reactions may be selected from known ones.

Useful amino protective groups include benzyloxycarbonyl (Z), tertiary butoxycarbonyl (Boc), isobornyloxycarbonyl and p-methoxybenzyloxycarbonyl.

Useful carboxyl protective groups include, for example, groups capable of forming methyl ester, ethyl ester, tertiary butyl ester and like lower alkyl esters, benzyl ester or p-methoxybenzyl ester.

Useful guanidino protective groups of arginine include, for example, 2,2,5,7,8-pentamethylchromone-6-sulfonyl (Pmc), 2,2,4,6,7-pentamethyldihydrobenzofuran-5-sulfonyl (Pbf), nitro, Z, Boc, p-toluenesulfonyl and the like.

The protective group elimination reaction can also be carried out by conventional methods such as catalytic reduction or methods using liquid ammonia and sodium, hydrogen fluoride, hydrogen bromide, hydrogen chloride, trifluoroacetic acid (TFA), acetic acid, methanesulfonic acid or the like.

The biotinylated phthalic acid ester derivative of formula (2) can be purified in a conventional manner using a variety of purification methods such as high performance liquid chromatography.

EXAMPLES

Reference Examples and Examples are given below to describe the present invention in more detail. It is to be understood that the invention is not limited to the embodiments described herein.

In the Reference Examples and Examples below, the following abbreviations and those mentioned above are used.

HATU: O-(7-azabenzotriazol-1-yl)-1,1,3,3-tetramethyl uronium hexafluorophosphate
DIEA: N,N-diisopropyl ethylamine
TFE: trifluoroethanol
TIPS: triisopropylsilane Reference Example 1
(1) Production of Diethyl 4-nitrophthalate (compound 401)
4-Nitrophthalic acid (2.0 g, 9.5 mmol) was dissolved in 30 ml of absolute ethanol and then 0.3 ml of concentrated sulfuric acid was added. The mixture was refluxed for 24 hours, and the solvent was evaporated under reduced pressure. The oily residue was dissolved in diethyl ether and washed three times with water and once with 10% $Na_2CO_3$ solution. The ether solution was dried over anhydrous sodium sulfate. After evaporation of the solvent, a light yellow crude solid was obtained. The crude product was recrystallized from cold ethanol. The resulting pale yellow crystals were dried in a vacuum desiccator overnight to give 1.9 g (75.3%) of diethyl 4-nitrophthalate (compound 401). $^1$H-NMR(CDCl$_3$); 8.62(1H, d, J=1.8 Hz), 8.39(1H, dd, J=8.8, 1.8 Hz), 7.85(1H, d, J=8.8Hz), 4.43(2H, q, J=7.3Hz), 4.42(2H, q, J=7.3Hz), 1.41(3H, t, J=7.3Hz), 1.40(3H, t, J=7.3Hz).

(2) Production of Diethyl 4-aminophthalate (compound 402)
Compound 401 (1.5 g, 5.6 mmol) was dissolved in 280 ml of benzene, and 3.4 g of purified zinc dust was added. Then 10 ml of concentrated hydrochloric acid was added in portions. After 15 min. of stirring at room temperature, another 3.4 g of zinc dust was added and the mixture was stirred at room temperature for 12 hours. 340 ml of cold water was added to the reaction mixture and the mixture was neutralized with 1N NaOH solution. The mixture was transferred to a separatory funnel and the benzene layer was removed. The aqueous layer was extracted with benzene. The combined benzene extracts were washed with water and dried over anhydrous sodium sulfate. After evaporation of the solvent, the pale yellow crude solid was obtained and purified by silica gel column chromatography (n-hexane: acetic acid =8:1) to give 1.1 g (80.6%) of diethyl 4-aminophthalate (compound 402).
mp: 95.6° C.; Elemental analysis for $C_{12}H_{15}NO_4$; Calcd.: C, 60.75; H, 6.37; N, 5.90; Found : C, 60.70; H, 6.33; N, 5.76; $^1$H-NMR(CDCl$_3$); 7.72(1H, d, J=8.4Hz), 6.73(1H, d, J=2.2Hz), 6.68(1H, dd, J=8.4, 2.2Hz), 4.36(2H, q, J=7.3Hz), 4.29(2H, q, J=7.3Hz), 4.11(2H, brs), 1.36(3H, t, J=7.3Hz), 1.34(3H, t, J=7.3Hz).

(3) Production of Dibutyl 4-nitrophthalate (compound 403)
4-nitrophthalic acid (2.0 g, 9.5 mmol) was dissolved in 30 ml of absolute ethanol and then 0.3 ml of concentrated sulfuric acid was added. The mixture was heated at 120° C. for 24 hours, and the solvent was evaporated under reduced pressure. The oily residue was dissolved in diethyl ether and washed three times with water and once with 10% $Na_2CO_3$ solution. The ether solution was dried over anhydrous sodium sulfate. After evaporation of the solvent, a light yellow crude solid was obtained. The crude product was purified by silica gel column chromatography (n-hexane: acetic acid =10:1) to give 2.1 g (68.4%) of di-n-butyl 4-nitrophthalate (compound 403).
$^1$H-NMR(CDCl$_3$); 8.61(1H, d, J=1.8Hz), 8.39(1H, dd, J=8.8, 1.8Hz), 7.84(1H, d, J=8.8Hz), 4.38(2H, q, J=7.3Hz), 4.36(2H, q, J=7.3Hz), 1.80–1.68(2H, m), 1.50–1.40(2H, m), 0.98(3H, t, J=7.3Hz), 0.90(3H, t, J=7.3Hz).

(4) Production of di-n-Butyl 4-aminophthalate (compound 404)
Compound 403 (1.5 g, 4.6 mmol) was dissolved in 230 ml of benzene and then 2.8 g of purified zinc dust was added. Concentrated hydrochloric acid (8.2 ml) was added in portions. After 15 minutes of stirring at room temperature, another 2.8 g of zinc dust was added and the mixture was stirred at room temperature for 12 hours. Then 280 ml of water was added to the reaction mixture and the mixture was neutralized with 1N NaOH solution. The mixture was transferred to a separatory funnel and the benzene layer was removed. The aqueous layer was extracted with benzene. The combined benzene extracts were washed with water and dried over anhydrous sodium sulfate. After evaporation of the solvent, the residue was purified by silica gel column chromatography (n-hexane: acetic acid =10:1) to give 980 mg (89.6%) of di-n-butyl 4-aminophthalate (compound 404).
Elemental analysis for $C_{16}H_{23}NO_4$; Calcd.: C, 65.51; H, 7.90; N 4.77; Found : C, 65.44; H, 7.90; N 4.65 ;
$^1$H-NMR(CDCl$_3$); 7.71(1H, d, J=8.4 Hz), 6.72(1H, d, J=2.2 Hz), 6.68(1H, dd, J=8.4, 2.2 Hz), 4.29(2H, t, J=7.3 Hz), 4.23(2H, t, J=7.3 Hz), 4.11(2H, brs), 1.75–1.62(2H, m), 1.50–1.36(2H, m), 0.95(6H, t, J=7.3 Hz).

(5) Production of Dicyclohexyl 4-nitrophthalate (compound 405)
4-nitrophthalic acid (2.0 g, 9.5 mmol) was dissolved in 30 ml of cyclohexanol, and then 0.3 ml of conc. sulfuric acid was added. The mixture was heated at 120° C. for 24 hours and the solvent was evaporated under reduced pressure. The oily residue was dissolved in diethyl ether and washed three times with water and once with 10% $Na_2CO_3$ solution. The ether solution was dried over anhydrous sodium sulfate. After evaporation of the solvent, the residue was purified by silica gel column chromatography (n-hexane: acetic acid =10:1) to give 2.3 g (65.5%) of dicyclohexyl 4-nitrophthalate (compound 405).

$^1$H-NMR(CDCl$_3$); 8.58(1H, d, J=1.8 Hz), 8.37(1H, dd, J=8.4, 1.8 Hz), 7.81(1H, d, J=8.4 Hz), 5.10–5.00(2H, m), 2.08–1.20(2H, m).

(6) Production of Dicyclohexyl 4-aminophthalate (compound 406)

Compound 405 (2.0 g, 5.3 mmol) was dissolved in 265 ml of benzene, and then 3.2 g of purified zinc dust was added. Concentrated hydrochloric acid (9.3 ml) was added in portions. After 15 minutes of stirring at room temperature, 3.2 g of zinc dust was added and the mixture was stirred at room temperature for 12 hours. Then 320 ml of water was added to the reaction mixture and the mixture was neutralized with 1N NaOH solution. The mixture was transferred to a separatory funnel and the benzene layer was removed. The aqueous layer was extracted with benzene. The combined benzene extracts were washed with water and dried over anhydrous sodium sulfate. After evaporation of the solvent, the residue was purified by silica gel column chromatography (n-hexane: acetic acid =10:1) to give 1.3 g (72.2%) of dicyclohexyl 4-aminophthalate (compound 406).

Elemental analysis for C$_{20}$H$_{27}$NO$_4$; Calcd.: C, 69.54; H, 7.88; N, 4.05; Found : C, 68.93; H, 7.77; N, 3.96;

$^1$H-NMR(CDCl$_3$); 7.70(1H, d, J=8.4 Hz), 6.70(1H, d, J=2.2 Hz), 6.65(1H, dd, J=8.4, 2.2 Hz), 5.03–4.89(2H, m), 4.08(2H, brs), 2.10–1.83(20H, m).

(7) Production of Benzyl n-butyl 4- (or 5-)nitrophthalate (compound 407)

4-Nitrophthalic anhydride (2.0 g, 10.4 mmol) was slowly added to a solution of 1.0 g of sodium n-butyrate and 1.0 g of n-butanol at a temperature not higher than 100° C. The mixture was kept at 90° C. to 100° C. for 10 minutes. Then 1.3 g of benzyl chloride and 36 mg of triethylamine were added to the solution, and the mixture was refluxed for 45 minutes. The reaction mixture was cooled and dissolved in diethyl ether. The ether solution as washed with water three times and then dried over nhydrous sodium sulfate. After evaporation of the solvent, the residue was purified by silica gel column chromatography (n-hexane: acetic acid =10:1) to 1.4 g (37.2%) of a mixture of benzyl n-butyl 4-nitrophthalate and benzyl n-butyl 5-nitrophthalate (1:1 mixture, compound 407).

$^1$H-NMR(CDCl$_3$); 8.62(1H, d, J=8.4 Hz), 8.61(1H, d, J=8.4 Hz), 8.40–8.35(2H, m), 7.88–7.36(12H, m), 5.38(4H, s), 4.24(2H, t, J=7.3 Hz), 4.22(2H, t, J=7.3 Hz), 1.72–1.25 (8H, m), 0.94(3H, t, J=7.3 Hz), 0.93(3H, t, J=7.3 Hz).

(8) Production of Benzyl n-butyl 4- (or 5-)aminophthalate (compound 408)

Compound 407 (1.2 g, 3.4 mmol) was dissolved in 170 ml of benzene, and then 2.1 g of purified zinc dust was added. Concentrated hydrochloric acid (6.0 ml) was added in portions. After 15 minutes of stirring at room temperature, another 2.1 g of zinc dust was added and the mixture was stirred at room temperature for 12 hours. Then 200 ml of water was added to the reaction mixture and the mixture was neutralized with 1N NaOH solution. The mixture was transferred to a separatory funnel and the benzene layer was removed. The aqueous layer was extracted with benzene. The combined benzene extracts were washed with water and dried over anhydrous sodium sulfate. After evaporation of the solvent, a pale yellow crude solid was obtained. The crude product was purified by silica gel column chromatography (n-hexane: acetic acid =10:1) to give 970 mg (80.0%) of a mixture of benzyl n-butyl 4-aminophthalate and benzyl n-butyl 5-aminophthalate (1:1 mixture, compound 408).

Elemental analysis for C$_{19}$H$_{21}$NO$_4$; Calcd.: C, 69.71; H, 6.47; N, 4.28; Found : C, 69.00; H, 6.41; N, 4.10;

$^1$H-NMR(CDCl$_3$); 7.76(1H, d, J=8.8 Hz), 7.72(1H, d, J=8.8 Hz), 7.45–7.30(10H, m), 6.74–6.65(4H, m), 5.33(2H, s), 5.27(2H, s), 4.18(2H,m), 4.17(2H, t, J=7.3 Hz), 4.13(2H, t, J=7.3 Hz), 4.09(4H, brs), 1.70–1.20(8H, m), 0.93(3H, t, J=7.3 Hz), 0.91(3H, t, J=7.3 Hz).

(9) Production of Ethyl n-hexyl 4- (or 5-)nitrophthalate (compound 409)

Sodium hydroxide (73 mg) was added to a solution of 2.0 g (10.4 mmol) of 4-nitrophthalic anhydride in n-hexanol. To the mixture were added 720 mg (15.8 mmol) of ethanol and a small amount of sulfuric acid. The mixture was refluxed for 5 hours and the reaction mixture was cooled and dissolved in diethyl ether. The ether solution was washed with water three times and then dried over anhydrous sodium sulfate. After evaporation of the solvent, the residue was purified by silica gel column chromatography (n-hexane: acetic acid =10:1) to give 1.2 g (36.5%) of a mixture of ethyl n-hexyl 4-nitrophthalate and ethyl n-hexyl 5-nitrophthalate (1:1 mixture, compound 409).

$^1$H-NMR(CDCl$_3$); 8.63–8.61(2H, m), 8.39(2H, dd, J=8.8, 1.8 Hz), 7.86(1H, d, J=8.8 Hz), 7.83(1H, d, J=8.8 Hz), 4.46–4.33(6H, m), 1.77–1.30(24H, m), 0.89–0.86(6H, m).

(10) Production of Ethyl n-hexyl 4-(or 5-)aminophthalate (compound 410)

Compound 409 (1 g, 3.1 mmol) was dissolved in 155 ml of benzene, and then 1.9 g of purified zinc dust was added. Concentrated hydrochloric acid (5.5 ml) was added in portions. After 15 minutes of stirring at room temperature, another 1.9 g of zinc dust was added and the mixture was stirred at room temperature for 12 hours. Then 180 ml of water was added and the mixture was neutralized with 1N NaOH solution. The mixture was transferred to a separatory funnel and the benzene layer was removed. The aqueous layer was extracted with benzene. The combined benzene extracts were washed with water and dried over anhydrous sodium sulfate. After evaporation of the solvent, a pale yellow crude solid was obtained and purified by silica gel column chromatography (n-hexane: acetic acid =10:1) to give 691 mg (76.1%) of a mixture of ethyl n-hexyl 4-aminophthalate and ethyl n-hexyl 5-aminophthalate (1:1 mixture, compound 410).

MS m/z: 293(M$^+$);

$^1$H-NMR(CDCl$_3$); 7.72 (2H, d, J=8.4 Hz), 6.73-6.72(2H, m), 6.69(2H, dd, J=8.4, 2.2 Hz), 4.40–4.20(8H, m), 4.11(4H, brs), 1.79–1.58(6H, m), 1.45–1.20(16H, m), 0.90–0.80(6H, m).

(11) Production of bis(2-ethylhexyl) 4-nitrophthalate (compound 411)

4-Nitrophthalic acid (2.0 g, 9.5 mmol) was dissolved in 30 ml of 2-ethylhexanol, and then 0.3 ml of sulfuric acid was added. The mixture was heated at 120° C. for 24 hours, and the solvent was evaporated under reduced pressure. Excess 2-ethyihexanol was removed from the oily residue by distillation. The oily residue was dissolved in diethyl ether and washed three times with water and once with 10%Na$_2$CO$_3$ solution. The ether solution was dried over anhydrous sodium sulfate. After evaporation of the solvent, the residue was purified by silica gel column chromatography (n-hexane: acetic acid =30:1) to give 2.3 g (65.5%) of bis(2-ethylhexyl) 4-nitrophthalate (compound 411.)

$^1$H-NMR(CDCl$_3$); 8.59(1H, d, J=2.6 Hz), 8.40(1H, dd, J=8.4, 2.6 Hz), 7.83(1H, d, J=8.4 Hz), 4.33–4.22(4H, m), 1.72–1.68(2H, m), 1.49–1.27(16H, m), 0.97–0.88(12H, m).

(12) Production of bis(2-ethylhexyl) 4-aminophthalate (compound 412)

Compound 411 (2.0 g, 5.3 mmol) was dissolved in 265 ml of benzene, and then 3.2 g of purified zinc dust was added.

Concentrated hydrochloric acid (9.3 ml) was added in portions. After 15 minutes of stirring at room temperature, another 3.2 g of zinc dust was added and the mixture was stirred at room temperature for 12 hours. Then 320 ml of water was added to the reaction mixture and the mixture was neutralized with 1N NaOH solution. The mixture was transferred to a separatory funnel and the benzene layer was removed. The aqueous layer was extracted with benzene. The combined benzene extracts were washed with water and dried over anhydrous sodium sulfate. After evaporation of the solvent, the residue was purified by silica gel column chromatography (n-hexane: acetic acid =15:1) to give 1.3 g (72.2%) of bis(2-ethylhexyl) 4-aminophthalate (compound 412).

$^1$H-NMR(CDCl$_3$); 7.70(1H, d, J=8.4 Hz), 6.72(1H, d, J=2.4 Hz), 6.68(1H, dd, J=8.4, 2.4 Hz), 4.22–4.13(6H, m), 1.72–1.62(2H, m), 1.43–1.22(6H, m), 0.94–0.87(12H, m).

Example 1

(1) Synthesis of Aminocapronyl-4-amino-diethyl Phthalate (formula (1): $R^1=R^2$=ethyl, m=5, Y=NH$_2$)

Boc-aminocaproic acid (69.4 mg, 0.3 mmol) was dissolved in 2 ml of THF. After cooling at −15° C., a mixed acid anhydride prepared from 30.6 μl (0.3 mmol) of N-methylmorpholine and 39.6 μl (0.3 mmol) of isobutylchloroformate, and a solution of 23.7 mg (0.1 mmol) of 4-amino-diethyl phthalate in 1 ml of THF were blended with the solution at −15° C. The mixture was stirred at room temperature for 18 hours.

After evaporation of the solvent, the residue was dissolved in ethyl acetate and washed with 5%NaHCO$_3$ and saturated saline. The ethyl acetate layer was dried over anhydrous sodium sulfate and filtered. The solvent was evaporated to give 74.4 mg of crude Boc-aminocapronyl-4-amino-diethyl phthalate as an oily substance.

The oily substance was dissolved in 2 ml of methanol and purified by reversed-phase HPLC for preparative isolation through the column "YMC-Pack D-ODS-5" (20×250 mm, product of YMC, Kyoto) using a 0.1% TFA/CH$_3$CN mixed solvent system (70/30→60/40; for 20 minutes) to give 31.0 mg of the desired protected compound.

The protected compound was treated with 1 ml of TFA at room temperature for 30 minutes and lyophilized to give 28.8 mg of the desired product.

Fab-mass spectrometry: Calcd. for $C_{18}H_{26}N_2O_5$: 350. Found: 351.

(2) Synthesis of H-Lys(Boc)-aminocapronyl-4-amino-diethyl Phthalate

Fmoc-Lys(Boc)-OH (12.3 mg, 0.027 mmol), HOBt (3.9 mg, 0.029 mmol) and the compound synthesized in (1) (8.8 mg, 0.025 mmol) were dissolved in 2 ml of THF. WSCD (5.6 μl, 0.032 mmol) was added at −10° C., and the mixture was stirred at room temperature for 18 hours. After evaporation of the solvent, the residue was dissolved in ethyl acetate and washed with 1N HCl, 5%NaHCO$_3$ and saturated saline. The ethyl acetate layer was dried over anhydrous sodium sulfate and the solvent was evaporated to give 19.5 mg of the desired protected compound.

The protected compound was treated with 2 ml of a solution of 20% piperidine in CH$_2$Cl$_2$ at room temperature for 10 minutes. After evaporation of the solvent, the residue was dissolved in ethyl acetate, washed with 5%NaHCO$_3$ and saturated saline and dried to give 18.0 mg of a crude product.

The crude product was dissolved in 2 ml of methanol and purified by reversed-phase HPLC for preparative isolation through the column "YMC-Pack D-ODS-5" (20×250 mm) using a 0.1% TFA/CH$_3$CN mixed solvent system (63/37→45/55; for 20 minutes) to give 7.4 mg of the desired product.

(3) Synthesis of Biotin-Arg(Pbf)-OH

Biotin (479 mg, 0.76 mmol), HATU (745 mg, 0.76 mmol) and H-Arg(Pbf)-Trt(2-Cl)-resin (1.0 g, 0.49 mmol) were suspended in 20 ml of DMF. DIEA (512 μl, 2.94 mmol) was added to the suspension, and the mixture was stirred at room temperature for 2 hours. The reaction mixture was filtered and washed with DMF and CH$_2$Cl$_2$ to give 1.12 g of biotin-Arg(Pbf)-Trt(2-Cl)-resin.

The resin of H-Arg(Pbf)-Trt(2-Cl)-resin was 1% divinylbenzene polystyrene copolymer (100–200 mesh).

The resulting protected peptide-resin was added to 20 ml of a mixed solution of acetic acid, TFE and CH$_2$Cl$_2$ (1:2:7) and treated at room temperature for 60 minutes. The resin was then removed by filtration. After evaporation of the solvent, the residue was solidified by addition of diethyl ether and reprecipitated from methanol-diethyl ether to give 340 mg of the desired product.

Fab-mass spectrometry: Calcd. for $C_{29}H_{44}N_6O_7S_2$: 652.834; Found: 653.389.

(4) Synthesis of Biotin-Arg-Lys-aminocapronyl-4-amino-diethyl Phthalate (formula (2): $R^1=R^2$=ethyl, $R^3$=biotin-Arg-Lys-NH, m=5)

H-Lys(Boc)-aminocapronyl-4-amino-diethyl phthalate (7.4 mg, 0.013 mmol) synthesized in (2), biotinyl-Arg(Pbf)-OH (8.8 mg, 0.013 mmol) synthesized in (3) and HOBt (2.2 mg, 0.016 mmol) were dissolved in 1 ml of DMF. WSCD (3.1 μl, 0.017 mmol) was added to the solution at −10° C. and the mixture was stirred at room temperature for 18 hours. The solvent was then evaporated. While the residue was cooled with ice, distilled water was added to solidify the residue. The solid was collected through centrifugation and dried to give 13.0 mg of a protected crude product.

The protected product was added to a solution containing 40 μl of distilled water and 40 μl of TIPS in 1.5 ml of TFA and treated at room temperature for 120 minutes. The reaction mixture was treated with diethyl ether to give 11.5 mg of a crude product.

The crude product was dissolved in 2 ml of 20% acetic acid and purified by reversed-phase HPLC for preparative isolation through the column "YMC-Pack D-ODS-5" (20× 250 mm) using a 0.1% TFA/CH$_3$CN mixed solvent system (75/25→65/35; for 30 minutes) to give 4.5 mg of the desired product.

Fab-mass spectrometry: Calcd. for $C_{40}H_{64}N_{10}O_9S$: 860; Found: 861.

Example 2

The following phthalic acid ester derivatives (2-1, 2-3, 2-5 and 2-7) were synthesized using the orresponding 4-amino-phthalic esters in a manner similar to the process described in Example 1 (1). Using these derivatives, the following biotinylated phthalic acid ester derivatives (2-2, 2-4, 2-6 and 2-8) were prepared in a manner similar to the process shown in Example 1 (3).

(2-1) Aminocapronyl-4-amino-dicyclohexyl Phthalate (formula (1): $R^1=R^2$=cyclohexyl, m=5, Y=NH$_2$)

Fab-mass spectrometry: Calcd. for $C_{26}H_{38}N_2O_5$: 458; Found: 459.

(2-2) Biotin-Arg-Lys-aminocapronyl-4-amino-dicyclohexyl Phthalate (formula (2): $R^1=R^2$=cyclohexyl, $R^3$=biotin-Arg-Lys-NH—, m=5)

Fab-mass spectrometry: Calcd. for $C_{48}H_{76}N_{10}O_9S$: 968; Found: 969.

(2-3) Aminocapronyl-4-amino-di-n-butyl Phthalate (formula (1): $R^1=R^2$=n-butyl, m=5, Y=NH$_2$)

Fab-mass spectrometry: Calcd. for $C_{22}H_{34}N_2O_5$: 406; Found: 407.

(2-4) Biotin-Arg-Lys-aminocapronyl-4-amino-di-n-butyl Phthalate (formula (2): $R^1=R^2$=n-butyl, $R^3$=biotin-Arg-Lys-NH—, m=5)

Fab-mass spectrometry: Calcd. for $C_{44}H_{72}N_{10}O_9S$: 916; Found: 917.

(2-5) Aminocapronyl-4-(or 5-)Amino-benzyl n-Butyl Phthalate (formula (1): $R^1$=benzyl (or n-butyl), $R^2$=n-butyl (or benzyl), m=5, Y=$NH_2$)

Fab-mass spectrometry: Calcd. for $C_{25}H_{32}N_2O_5$: 440; Found: 441.

(2-6) Biotin-Arg-Lys-aminocapronyl-4-(or 5-)Amino-benzyl-n-butyl Phthalate (formula (2): $R^1$=benzyl (or n-butyl), $R^2$=n-butyl (or benzyl), $R^3$=biotin-Arg-Lys-NH—, m=5)

Fab-mass spectrometry: Calcd. for $C_{47}H_{70}N_{10}O_9S$: 950; Found: 951.

(2-7) Aminocapronyl-4-(or 5-)Amino-ethyl n-heptyl Phthalate (formula (1): $R^1$=ethyl (or n-heptyl), $R^2$=n-heptyl (or ethyl), m=5, Y=$NH_2$)

Fab-mass spectrometry: Calcd. for $C_{23}H_{36}N_2O_5$: 420; Found: 421.

(2-8) Biotin-Arg-Lys-aminocapronyl-4-(or 5-)Amino-ethyl n-heptyl Phthalate (formula (2): $R^1$=ethyl (or n-heptyl), $R^2$=n-heptyl (or ethyl), $R^3$=biotin-Arg-Lys-NH—, m=5)

Fab-mass spectrometry: Calcd. for $C_{45}H_{74}N_{10}O_9S$: 930; Found: 931.

Example 3

(1) Synthesis of Monoglutaryl-4-amino-di(2-ethylhexyl) Phtalate (formula (1): $R^1=R^2$=2-ethylhexyl, m=3, Y=COOH)

4-Amino-di(2-ethylhexyl)phtalate (101.4 mg, 0.25mmol) and glutaric anhydride (85.6 mg, 0.75 mmol) were dissolved in 5 ml of THF. The solution was refluxed for 8 hours and further stirred at room temperature for 18 hours. After evaporating the solvent, the residue was dissolved in ethyl acetate and washed with $H_2O$ and saturated saline. The ethyl acetate layer was dried over anhydrous sodium sulfate and filtered and the solvent was evaporated to give 120 mg of the desired product.

Fab-mass spectrometry: Calcd. for $C_{29}H_{45}NO_7$: 519; Found: 520.

(2) Synthesis of H-Arg(Pbf)-NHNH-biotin

To 5 ml of a solution of Fmoc-Arg(Pbf)-OH (648.8 mg, 1 mmol), HOBt (135.1 mg, 1.2 mmol) and biotin-$N_2H_3$ (258.3 mg, 1 mmol) in DMF was added WSCD (176.4 μp, 1.2 mmol) at −10° C. The mixture was stirred at room temperature for 18 hours. After evaporation of the solvent, the residue was dissolved in ethyl acetate and washed with 1NHCl, 5%$NaHCO_3$ and saturated saline. The ethyl acetate layer was dried over anhydrous sodium sulfate and filtered. After evaporation of the solvent, petroleum ether was added to solidify the residue. The solid was reprecipitated from ethyl acetate-petroleum ether to give 800.2 mg of Fmoc-Arg(Pbf)-NHNH-biotin.

The resulting compound (800.2 mg) was treated with a solution of 20% piperidine in $CH_2Cl_2$ at room temperature for 10 minutes. After evaporation of the solvent, the residue was dissolved in ethyl acetate, washed with $H_2O$ and saturated saline. The ethyl acetate layer was dried over anhydrous sodium sulfate and filtered. The filtrate was solidified by evaporation of the solvent.

The crude product was dissolved in methanol. The insoluble substances were removed by filtration. The solvent was evaporated from the filtrate to give 366.8 mg of the desired compound.

(3) Synthesis of H-Arg(Pbf)-Arg(Pbf)-NHNH-biotin

The compound synthesized in (2) (366.8 mg, 0.55 mmol), Fmoc-Arg(Pbf)-OH (374.7 mg, 0.58 mmol) and HOBt 89.2 mg (0.66 mmol) were dissolved in 5 ml of DMF. WSCD (176.4 μl, 0.66 mmol) was added at −10° C. and the mixture was stirred at room temperature for 18 hours. The solvent was then evaporated. While the residue was cooled with ice, $H_2O$ was added to solidify the residue. The solid was reprecipitated from methanol-diethyl ether to give 635.2 mg of Fmoc-Arg(Pbf)-Arg(Pbf)-NHNH-biotin.

This compound (635.2 mg) was treated with a solution of 20% piperidine in $CH_2Cl_2$ at room temperature for 10 minutes and washed with $H_2O$ and saturated saline. The resulting mixture was dried over anhydrous sodium sulfate and filtered and the solvent was evaporated to give a crude product.

The crude product was dissolved in methanol and then the insoluble substances were removed by filtration. After evaporation of the solvent, the residue was solidified by addition of diethyl ether to give 503.2 mg of the desired compound.

(4) Reaction Product of Compound (1) and Biotin-Arg-Arg (formula (2): $R^1=R^2$=2-ethylhexyl, $R^3$=-CO-Arg-Arg-NHNH-biotin, m=3)

H-Arg(Pbf)-Arg(Pbf)-NHNH-biotin synthesized in (3) (21.5 mg, 0.02 mmol), monoglutaryl-4-amino-di(2-ethylhexyl)phthalate synthesized in (1)(10.4 mg, 0.02 mmol) and HOBt (5.9 mg, 0.04 mmol) were dissolved in 2 ml of DMF. WSCD (7.1 μl, 0.04 mmol) was added to the solution at −10° C. and the mixture was stirred at room temperature for 18 hours. The solvent was then evaporated.

While the residue was cooled with ice, $H_2O$ was added to solidify the residue, giving 31.5 mg of a crude product (Arg-protected compound).

The crude product (31.5 mg) was treated with 3.85 ml of TFA containing 0.15 ml of TIPS at room temperature for 120 minutes and diether ether was then added to give 12.9 mg of a crude product.

The crude product (12.9 mg) was dissolved in 2 ml of 10% acetic acid and purified by reversed-phase HPLC for preparative isolation through the column "YMC-Pack D-ODS-5" (20×250 mm) using a 0.1% TFA/$CH_3CN$ mixed solvent system (50/50→30/70; for 30 minutes) to give 6.5 mg of the desired compound.

Fab-mass spectrometry: Calcd. for $C_{51}H_{85}N_{13}O_{10}S$: 1072; Found: 1073.

Example 4

Preparation of Antiserum

Aminocapronyl-4-amino-diethyl phthalate synthesized in Example 1 (1) (7.1 mg) was dissolved in 1 ml of $H_2O$. The solution was mixed with a solution of keyhole limpet hemocyanin (KLH; 10 mg; Pierce Chemical Company) in 0.1M PBS buffer (pH 6.0). DMS (dimethyl suberimidate. 2HCl: 70 mg; Pierce Chemical Company) was added and the reaction was allowed to proceed at room temperature for 30 minutes.

The reaction mixture was desalted by gel filtration and the resulting KLH-aminocapronyl-4-amino-diethyl phthalate complex was used as an immunogen in the following process.

The immunogen (2 mg) was mixed with 1 ml of 50% polyvinylpyrrolidone (Merck & Co., Ltd.), and then 3 ml of Freund's complete adjuvant (Calbiochem) was added to form an emulsion.

Two rabbits (Japan white, male, body weight: 2.1–2.5 kg) were intradermally injected with the above emulsion in an amount of 1 mg of antigen per rabbit. For additional immunizations, the rabbits were injected with about 0.5 mg of antigen another 6 times at an interval of 2 weeks. One week after the final immunization, the rabbits, whose blood contained a sufficient titer of antiserum, were exsanguinated. The collected blood was kept at 37° C. for 1 hour and then at 4° C. overnight. The blood was centrifuged at 3000 rpm (rotation/minute) and the resulting antiserum (RY778) was lyophilized.

Example 5

Enzyme Immunoassay (ELISA) for Diethyl Phthalate

An ELISA system of the present invention for diethyl phthalate was designed in the following manner.

Diethyl phthalate was diluted as follows. A solution (857 µg/mL) of 12 mg of diethyl phthalate in 15.7% DMSO was 10-fold diluted with PBS buffer to give a standard solution (85.7 µg/ml). Five-fold dilution of the standard solution was repeated to give solutions of various concentrations (17.1 µg/ml, 3.4 µg/ml, 0.69 µg/ml, 0.137 µg/ml, 0.027 µg/ml and 0.005 µg/ml). These solutions were used as diluted standard antigen solutions.

Biotin-Arg-Lys-aminocapronyl-4-amino-diethyl phthalate synthesized in Example 1 (4) was diluted to 2 ng/ml with PBS buffer and used as a labeled antigen solution.

Antiserum RY778 (anti-phthalic acid ester antibody) synthesized in Example 4 was diluted 10,000-fold with PBS buffer (containing 0.1% BSA and 0.1% Tween 20) and used as an antibody solution.

Goat anti-rabbit IgG (Jackson Immuno Research) was diluted 200-fold with 0.1M phosphate buffer (pH8.0), and 100 µl of the diluted IgG was pipetted into each well of a 96-well microtiter plate (Maxi Sorp, Nunc). The plate was allowed to stand at 25° C. for 18 to 20 hours and then the supernatant was removed. Subsequently, 340 µl of Block Ace (Dainippon Pharmaceutical Co., Ltd.) was pipetted into each well and the plate was allowed to stand at 25° C. for 18 to 20 hours whereby blocking was completed.

After the plate was washed with a wash solution (0.15M NaCl containing 0.1% Tween 20) 5 times, 50 µl of a diluted standard antigen solution or sample, 50 µl of the labeled antigen solution and 100 µl of the antibody solution were added to each well. The culture was incubated at 4° C. for 18 to 20 hours. The plate was washed 3 times with 0.3 ml of the wash solution, and then 0.1 ml of a streptavidin-horseradish peroxidase conjugate (×2500) was added. After incubation at room temperature for 1.5 hours, the plate was washed with 0.3 ml of the wash solution 4 times and then a tetramethyl benzidine-containing colorant (0.1 ml, product of Sigma) was added. After 30 minutes of coloring, 2N sulfuric acid was added to stop the reaction. Absorbance at 450 nm was measured.

A standard curve for diethyl phthalate was obtained from the results of the diluted standard antigen solutions (FIG. 1). In FIG. 1, the ordinate denotes absorbance (at 450 nm) and the abscissa denotes standard antigen concentration (ng/ml).

FIG. 1 indicates that the minimum detectable level of diethyl phthalate is 50 pg/ml.

The ELISA system of the invention was tested for assay precision. Intra and inter-assay coefficients of variation were 2.3% and 5.8%, respectively.

Example 6

Cross-reactivity Test for Diethyl Phthalate

The cross-reactivity of the antibody of the invention with diethyl phthalate and structurally similar compounds was tested using the ELISA system described in Example 5. Table 1 shows the results.

TABLE 1

| Test compound | $IC_{50}$ (ng/ml) | Cross-reactivity (%) |
|---|---|---|
| Diethyl phthalate | 0.546 | 100 |
| Dimethyl phthalate | 98.178 | 0.556 |
| Dibutyl phthalate | 3893.432 | 0.014 |
| Di(2-ethylhexyl)phtalate | — | <0.001 |
| Phthalic acid | — | <0.001 |
| Benzoic acid | — | <0.001 |
| Ethyl benzoate | 4391.316 | 0.012 |
| Ethyl formate | 3001.226 | 0.018 |
| Ethyl acetate | 4480.033 | 0.012 |
| Ethyl succinate | 3534.158 | 0.015 |
| Estradiol | 15053.168 | 0.004 |
| Dimethyl stilbestrol | — | <0.001 |

In the immunoassay, the antibody of the invention showed high reactivity with diethyl phthalate. With respect to cross-reactivity with other structurally similar phthalic acid esters, the cross-reactivity with dimethyl phthalate was about 0.56% and that with dibutyl phthalate about 0.01%. The cross-reactivities with di(2-ethylhexyl)phthalate and with phthalic acid were less than 0.001%.

The results clearly show that the reactivity of the antibody of the invention is highly specific to the side chain structure of diethyl phthalate.

The cross-reactivity of the antibody of the invention with compounds having structures related to phthalic acid esters was very low. That is, the cross-reactivity with benzoic acid was less than 0.001%, and the cross-reactivities with ethyl benzoate, ethyl formate, ethyl acetate and ethyl succinate were 0.012%, 0.018%, 0.012% and 0.015%, respectively.

The cross-reactivities with estradiol and dimethyl stilbestrol were tested because like diethyl phthalate, they are endocrine disrupting chemicals. The results indicate that the antibody of the invention does not show substantial cross-reactivity with these two compounds.

Cross-reactivity (%) is defined as the molar concentration of each test antigen, relative to the concentration of diethyl phthalate (calculated as 100%), at $B/B_0=50$.

Example 7

In this Example, the amount of diethyl phthalate leached from various commercially available plastic disposable gloves was measured using the immunoassay of the invention. Such elusion from disposable gloves has recently been in the news. Measurements were taken in the following manner.

Each of the disposable gloves was cut into pieces (weighing 0.05 to 0.4 g). 3.0 ml of 70% ethanol was added to the pieces and an extraction procedure was carried out at room temperature overnight. The extract was evaporated using a centrifugal evaporator to remove the ethanol and then dissolved in 3.0 ml of a buffer for ELISA. The resulting extract was used as a test sample. The amount of diethyl phthalate in the test sample was measured according to the method described in Example 5.

Table 2 shows the results.

TABLE 2

| Gloves | Amount of diethyl phthalate (ng/gram glove) |
|---|---|
| Product A | 795.064 |
| Product B | 704.811 |
| Product C | 31.968 |
| Product D | 151.320 |
| Product E | 265.488 |
| Product F | 526.869 |
| Product G | 124.874 |
| Product H | 160.068 |
| Product I | 80.633 |
| Product J | 38.566 |

Diethyl phthalate was detected in all the 70% ethanol extracts of the disposable plastic gloves, which indicates that the immunoassay of the invention can accurately measure diethyl phthalate.

Example 8

Enzyme Immunoassay (ELISA) for Benzyl n-butyl Phthalate

An ELISA system of the invention for benzyl n-butyl phthalate was designed in a manner similar to that of Example 5, using benzyl n-butyl phthalate (product of Kanto Chemical Co., Inc.) as a standard antigen, using biotin-Arg-Lys-aminocapronyl-4-(or 5-)amino-benzyl n-butyl phthalate of Example 2 (2-6) as a labeled antigen and using antiserum RY850 (10,000-fold diluted) as an antiserum. The antiserum RY850 was prepared as in Example 4, but the aminocapronyl-4-(or 5-)amino-benzyl n-butyl phthalate of Example 2 (2-5) was used in place of aminocapronyl-4-amino-diethyl phthalate.

Figure 2:
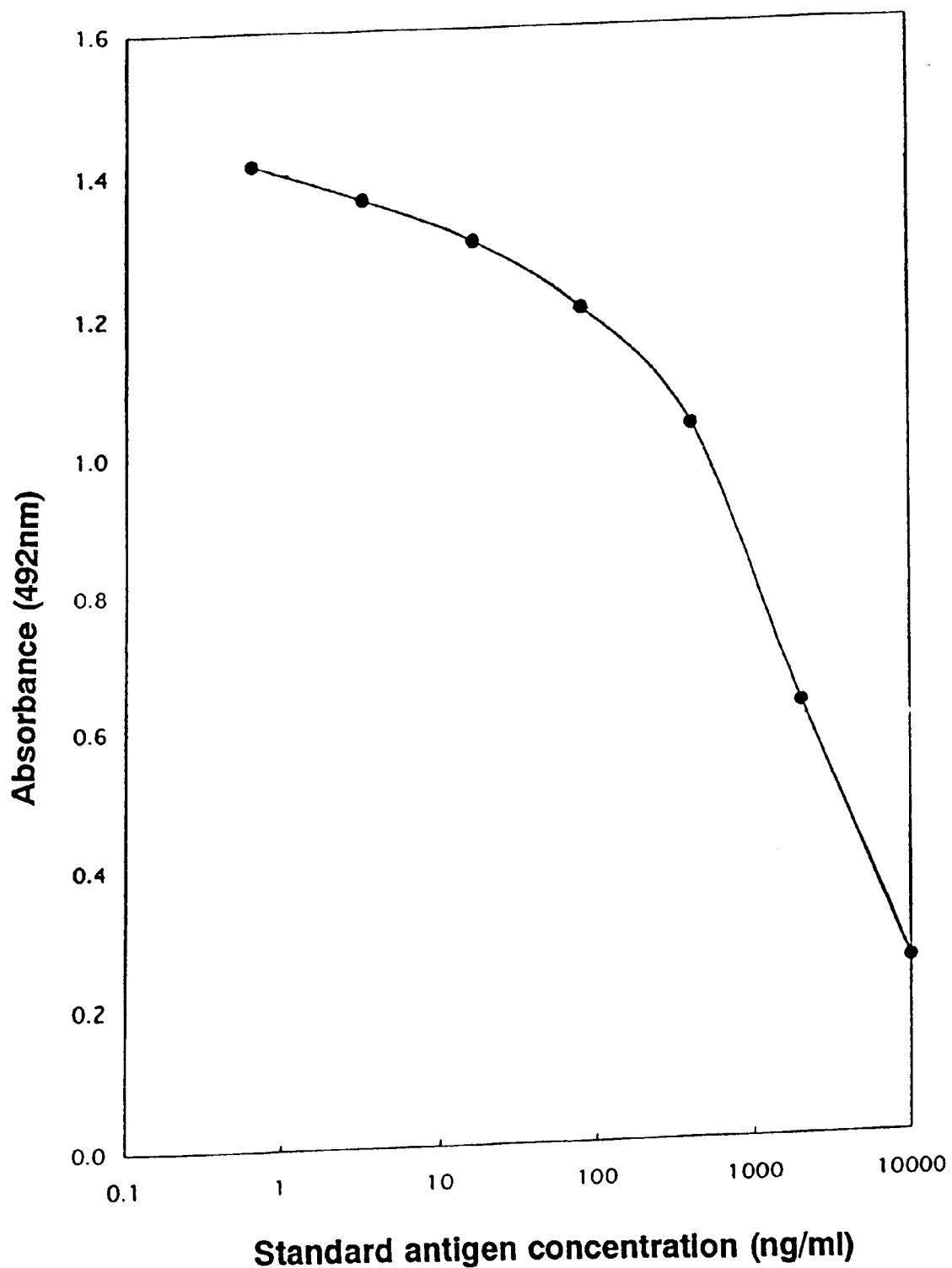
FIG. 2 is an enzyme immunoassay standard curve for benzyl n-butyl phthalate.

A standard curve for benzyl n-butyl phthalate was obtained (FIG. 2). In FIG. 2, the ordinate denotes absorbance (at 492 nm) and the abscissa denotes standard antigen concentration (ng/ml).

FIG. 2 indicates that levels of benzyl n-butyl phthalate from 0.64 to 10,000 ng/mL are measurable with this system.

Example 9

Cross-reactivity Test Using the ELISA System for Benzyl n-butyl Phthalate

The cross-reactivity of the antibody of the invention with benzyl n-butyl phthalate and structurally similar compounds was determined using the ELISA system described in Example 8.

The cross-reactivities with dimethyl phthalate, diethyl phthalate, di(2-ethylhexyl)phtalate, phthalic acid, benzoic acid, ethyl benzoate, ethyl formate, ethyl acetate, diethyl succinate, dietylstilbestrol, monobutyl phthalate and bisphenol A were all 1% or less. The cross-reactivity with nonylphenol was 2.3% and that with estradiol was 3.5%, indicating that the antibody does not substantially crossreact with any of these compounds. The cross-reactivity with di-n-butyl phthalate was 38.9%.

Example 10

Enzyme Immunoassay (ELISA) for di-n-butyl Phthalate

An ELISA system of the invention for di-n-butyl phthalate was designed in a manner similar to that of Example 5, using di-n-butyl phthalate (product of Wako Pure Chemical Industries, Inc.) as a standard antigen, using biotin-Arg-Lys-aminocapronyl-4-amino-di-n-butyl phthalate of Example 2 (2-4) as a labeled antigen and using antiserum RY849 (10,000-fold diluted) as an antiserum. The antiserum RY849 was prepared as in Example 4, but the aminocapronyl-4-amino-di-n-butyl phthalate of Example 2 (2-3) was used in place of aminocapronyl-4-amino-diethyl phthalate of Example 4.

Figure 3:
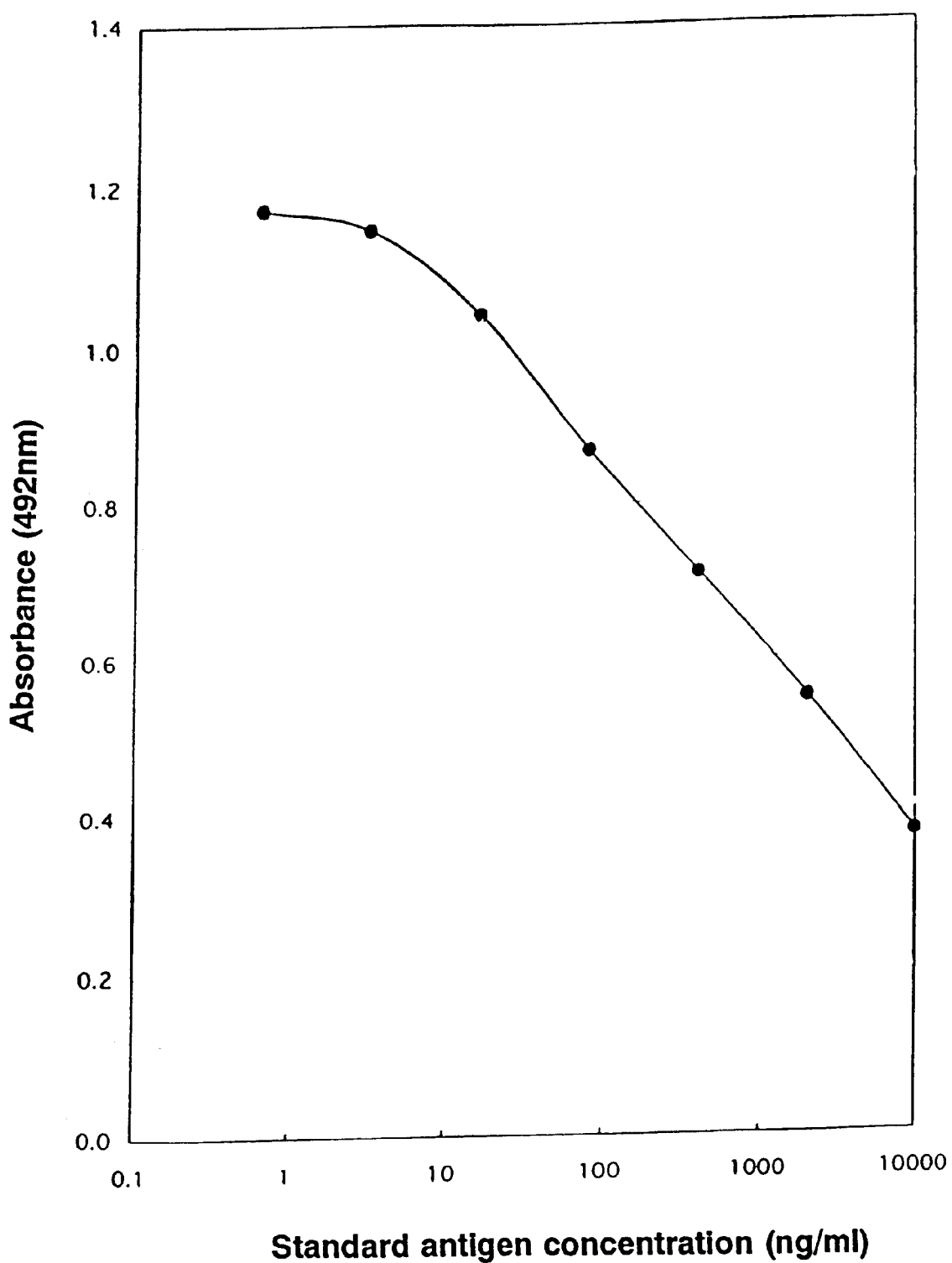
FIG. 3 is an enzyme immunoassay standard curve for di-n-butyl phthalate.

A standard curve for di-n-butyl phthalate was obtained (FIG. 3).

FIG. 3 indicates that levels of di-n-butyl phthalate from 0.64 to 10,000 ng/mL are measurable with this system.

Example 11

Cross-reactivity Test Using the ELISA System for di-n-butyl Phthalate

The cross-reactivity of the antibody of the invention with di-n-butyl phthalate and structurally similar substances was determined using the ELISA system described in Example 10.

The cross-reactivities with di(2-ethylhexyl)phthalate, phthalic acid, benzoic acid, ethyl benzoate, ethyl formate, ethyl acetate, diethyl succinate, monobutyl phthalate and bisphenol A were all less than 1%.

The cross-reactivities with dimethyl phthalate, diethyl stilbestrol, diethyl phthalate, nonylphenol and 17β-estradiol were 1.2%, 1.5%, 4%, 3.4%, 1.2%, respectively, which indicates that the antibody does not substantially crossreact with any of these compounds. The cross-reactivity with benzyl n-butyl phthalate was 100%.

What is claimed is:

1. An antigen for the production of an anti-phthalic acid ester antibody, which comprises a conjugate of a carrier protein and a phthalic acid ester derivative represented by the formula

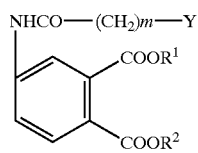

(1)

wherein $R^1$ and $R^2$ may be the same or different and are hydrogen, alkyl, cycloalkyl or phenylalkyl, with the proviso that both of $R^1$ and $R^2$ are not hydrogen simultaneously; m is an integer from 1 to 5; and Y is amino or carboxyl.

2. An anti-phthalic acid ester antibody produced using the antigen of claim 1.

3. A biotinylated phthalic acid ester derivative represented by the formula

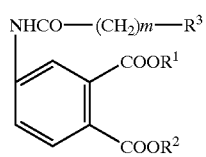

(2)

wherein $R^1$ and $R^2$ may be the same or different and are hydrogen, alkyl, cycloalkyl or phenylalkyl, with the proviso that both of $R^1$ and $R^2$ are not hydrogen simultaneously; m is an integer from 1 to 5; and $R^3$ is biotin-$(R^4)_n$—NH— or —CO—$(R^4)_n$—NHNH-biotin wherein the $R^4$s may be the same or different and are an Arg residue or a Lys residue, and n is an integer from 1 to 3.

4. A method for assaying phthalic acid esters in a sample by an immunoassay technique, which comprises measuring the phthalic acid esters contained in the sample using the anti-phthalic acid ester antibody of claim 2.

5. The method according to claim 4 wherein the immunoassay technique utilizes the biotinylated phthalic acid ester derivative of claim 3 as a labeled compound.

* * * * *